(12) United States Patent
Johnson (10) Patent No.: US 10,231,795 B1
(45) Date of Patent: Mar. 19, 2019

(54) PORTABLE MONITORING SYSTEM TRANSPORT CASE

(71) Applicant: Kenneth R. Johnson, Dallas, TX (US)

(72) Inventor: Kenneth R. Johnson, Dallas, TX (US)

(*) Notice: Subject to any disclaimer, the term of this patent is extended or adjusted under 35 U.S.C. 154(b) by 0 days.

(21) Appl. No.: 15/730,496

(22) Filed: Oct. 11, 2017

(51) Int. Cl.
| | |
|---|---|
| *A47F 5/00* | (2006.01) |
| *A61B 50/26* | (2016.01) |
| *A47B 96/06* | (2006.01) |
| *A47B 43/00* | (2006.01) |
| *F16M 11/24* | (2006.01) |
| *A47B 45/00* | (2006.01) |

(52) U.S. Cl.
CPC .......... *A61B 50/26* (2016.02); *A47B 43/003* (2013.01); *A47B 45/00* (2013.01); *A47B 96/06* (2013.01); *F16M 11/24* (2013.01); *F16M 2200/02* (2013.01)

(58) Field of Classification Search
CPC .......... A61B 50/26; A45C 5/14; A45C 13/28
USPC .......... 248/125.8; 280/47.19, 47.26, 638, 652
See application file for complete search history.

(56) References Cited

U.S. PATENT DOCUMENTS

| | | | |
|---|---|---|---|
| 6,543,796 B1 | 4/2003 | Johnson | |
| 7,389,997 B2 | 6/2008 | Johnson | |
| 7,946,609 B2* | 5/2011 | Johnson | A45C 5/14 |
| | | | 280/47.19 |
| 10,034,537 B2* | 7/2018 | Long, Jr. | A45C 13/262 |

* cited by examiner

*Primary Examiner* — Todd M Epps (57) ABSTRACT

A portable transport system for containing and transporting monitoring system components includes a case for enclosing the monitoring system components. A collapsible desk assembly telescopes between a collapsed position wherein the entire collapsible desk assembly is substantially contained within the case and an open position. The collapsible desk assembly includes a desk shelf that extends outward from the collapsible desk assembly in the open position and folds down within the case in the collapsed position. A collapsible monitoring component assembly telescopes between a collapsed position wherein the entire collapsible monitoring component assembly is substantially contained within the case and an open position. The collapsible monitoring component assembly includes a component bracket mounting handle for interfacing the monitoring system components with the collapsible monitoring component assembly. The component bracket mounting handle moves the monitoring system components between a raised position and a lowered position. The collapsible desk assembly and the collapsible monitoring component assembly are contained substantially within the case in the collapsed position.

23 Claims, 9 Drawing Sheets

PORTABLE MONITORING SYSTEM TRANSPORT CASE

TECHNICAL FIELD

The present invention relates to portable, transportable monitoring systems, and more particularly, to a carrying case system for containing a portable monitoring system.

BACKGROUND

Monitoring systems in a large variety of technical areas include a variety of electronic equipment for testing, monitoring, checking various statuses and current states of a variety of parameters. In many situations, the monitoring systems comprise large equipment that is located at a particular site and the item or person to be monitored is brought to the site for testing and monitoring. However, due to inability or inconvenience of moving some test items/subjects to a centralized testing location, there has arisen the need for portable monitoring systems that allow the monitoring devices to be transported to a remote location to enable monitoring of a test items/subjects. The monitoring system may be utilized for testing a variety of items/subjects such as electronic device testing, medical testing, automobile testing, computer system testing, etc. The monitoring systems often require a number of monitoring components in order to perform an appropriate test analysis. This requires transporting the monitoring components to the remote location to perform the necessary tests. Independently moving each of the monitoring components to a remote location is a time and labor intensive process. Thus, there is a need for providing a manner for easily transporting monitoring components to a remote location for performing testing operations.

SUMMARY

The present invention, as disclosed and described herein, in one aspect thereof, comprises a portable transport system for containing and transporting monitoring system components that includes a case for enclosing the monitoring system components. A collapsible desk assembly telescopes between a collapsed position wherein the collapsible desk assembly is substantially contained within the case and an open position. The collapsible desk assembly includes a desk shelf that extends outward from the collapsible desk assembly in the open position and folds down within the case in the collapsed position. A collapsible monitoring component assembly telescopes between a collapsed position wherein the collapsible monitoring component assembly is substantially contained within the case and an open position. The collapsible monitoring component assembly includes a component bracket mounting handle for interfacing the monitoring system components with the collapsible monitoring component assembly. The component bracket mounting handle moves the monitoring system components between a raised position and a lowered position. The collapsible desk assembly and the collapsible component monitoring assembly are contained substantially within the case in the collapsed position.

BRIEF DESCRIPTION OF THE DRAWINGS

For a more complete understanding, reference is now made to the following description taken in conjunction with the accompanying Drawings in which.

DETAILED DESCRIPTION

Referring now to the drawings, wherein like reference numbers are used herein to designate like elements throughout, the various views and embodiments of a portable monitoring system transport case are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Figure 1:
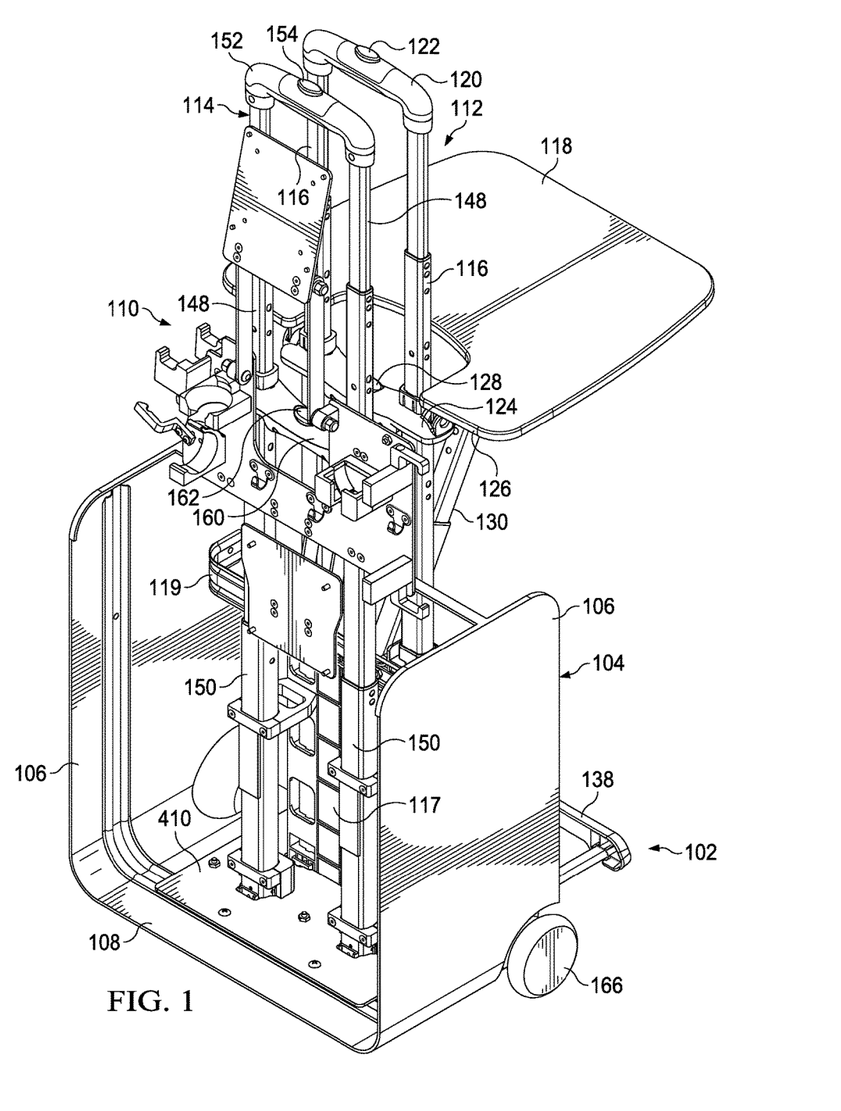
FIG. 1 illustrates a perspective view of a monitoring system transport case.

FIG. 1 illustrates a perspective view of the portable monitoring system transport case 102. The case 102 includes a case shell 104 that encloses all of the system components. The case shell 104 may be made of fabric, metal, plastic, etc. and appears to be a standard carrying case similar to existing luggage/briefcase systems. While the illustration of FIG. 1 illustrates only the side panels 106 and bottom panel 108 of the case shell 104, additional front, back and top panels also make up the case shell 104 in order to substantially enclose components within the case shell 102 for transport of the complete product.

Figure 2:
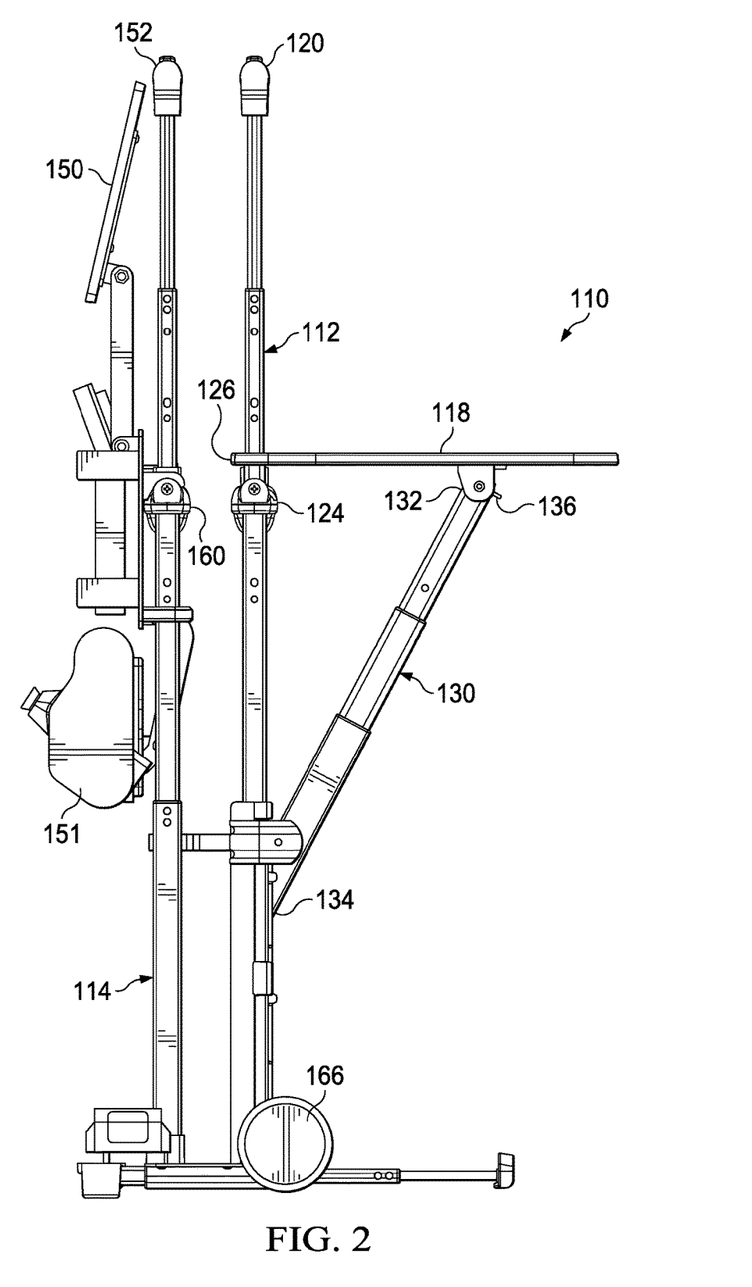
FIG. 2 illustrates a side view of a component support frame.

Contained within the case shell 104 is a collapsible monitoring component support frame 110. The monitoring component support frame 110 is also illustrated in FIG. 2 with the case shell 104 completely removed. It should also be realized that in an alternative embodiment the system may include only the monitoring component support frame 110 without the case shell 102. The monitoring component support frame 110 includes a collapsible desk assembly 112 and a collapsible monitoring component assembly 114. The collapsible desk assembly 112 consists of first and second telescoping members 116 that move between a collapsed position for transport and an extended position for use of an associated desk shelf 118. The collapsible desk assembly is similar to that of U.S. Pat. No. 7,946,609, which is incorporated herein by reference in its entirety. The first and second telescoping members 116 may comprise two or more tubes of progressively smaller sizes that telescope within one another as the members 116 are collapsed. A desk assembly support plate 117 includes slots for receiving the first and second telescoping members 116 to support them and anchor the collapsible desk assembly 112 to the case shell 104. The desk assembly support plate 117 maintains the first and second telescoping members 116 a fixed distance from each other. A support bracket 119 is connected to the desk assembly support plate 117 and extends outward from the sides thereof enabling the desk assembly support plate to be connected to the side panels 106 of the case shell 104.

A handle 120 with an actuator button 122 allows the first and second telescoping members 116 to be raised and lowered between the collapsed position and the extended position. The handle 120 is located inside of the case shell 104 in the collapsed position. The actuator button 122 disengages a locking mechanism that automatically locks the first and second telescoping members 116 into the extended position when the handle 120 is raised from the collapsed position. The locking mechanism automatically engages when the first and second telescoping members 116 are moved to the extended position. The locking mechanism in one embodiment may comprise a spring loaded locking tab or detent that inserts into an opening in the first and second telescoping members 116 as the first and second telescoping members are raised to the extended position. The first and second telescoping members 116 may include one or more intermediate extended positions between the collapsed position and the extended position in which the first and second telescoping members 116 may be configured in a locked position. The actuator button 122 on the handle 120 is also used for disengaging the locking mechanism from these intermediate extended positions.

The desk shelf 118 comprises a flat surface that may be pivoted to an open position perpendicular to the first and second telescoping members 116 from a collapsed position wherein the desk shelf 118 lies substantially parallel to and against the first and second telescoping members 116. A desk handle 124 is located between the handle 120 and the end of the telescoping member 116 contained within support plate 117 and slidably engages the telescoping member 116 running through the desk handle 124. The desk handle 124 enables a back edge 126 of the desk shelf 118 to be moved between a lowered position and a raised position. The desk handle 124 includes an actuator button 128 that disengages a locking mechanism that automatically locks the desk handle 124 in the raised position. The actuator button 128 when depressed enables the desk handle 124 to be moved from the raised position to the lowered position. The locking mechanism may comprise in one embodiment a spring loaded tab or detent mechanism within the handle that is biased to insert within an opening within the first and second telescoping members 116 to automatically lock the desk handle 124 in the raised position and to retract from the opening when the actuator button 128 is engaged enabling the desk handle to be lowered to the lowered position.

The back edge 126 of the desk shelf 118 is pivotally connected to the desk handle 124 to enable the desk shelf 118 to pivot between the open position perpendicular to the first and second telescoping members 116 and the collapsed position parallel to the first and second telescoping members. When in the open position, the desk shelf 118 is held in position by desk support member 130. The desk support member 130 comprises a telescoping member having a first end 132 pivotally connected to a bottom side of the desk shelf 118 and a second end 134 pivotally connected to the desk assembly support plate 117. In the collapsed position, one or more tubular members of the desk support member 130 collapse within each other enabling the desk shelf 118 to lie perpendicular and next to the first and second telescoping members 116. In the open position, the desk support member 130 fully extends and locks into the open position to support the desk shelf 118 perpendicular to the first and second telescoping members 116. A release lever 136 enables the locking mechanism maintaining the desk support member 130 in the locked open position to disengage and enable the desk shelf 118 to be lowered to the collapsed position. The desk shelf 118 when in the open position may be utilized as a writing surface, lap top desk or shelf for placing paperwork or other materials.

Figure 3:
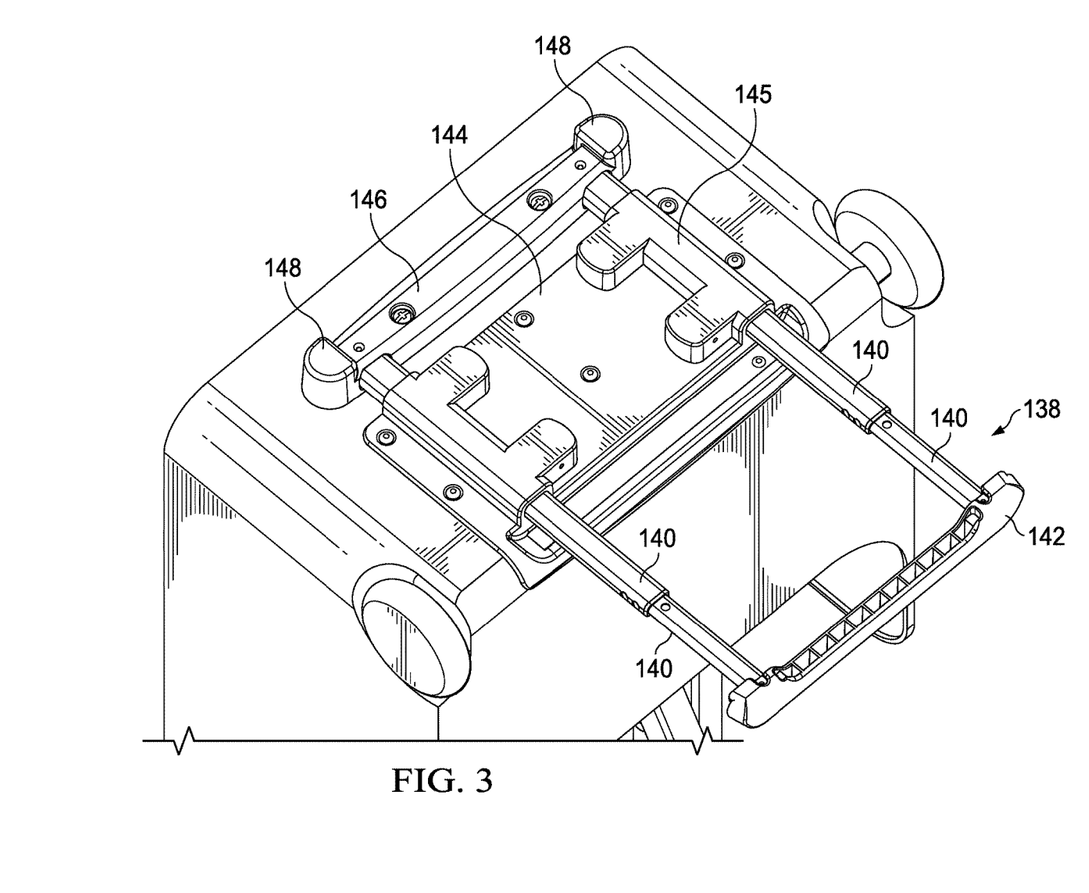
FIG. 3 illustrates a perspective view of the extendable support foot.

Referring now to FIG. 3, the transport case 102 is prevented from toppling due to weight placed on the desk shelf 118 by an extendable support foot 138. The extendable support foot 138 consists of a pair of telescoping members 140 connected by support crossmember 142. A first end of the telescoping members 140 are connected to the support crossmember 142 and a second end of the telescoping members are secured through a pair of tunnels 145 within a base support plate 144 into foot support piece 146 located on the bottom panel 108 of the case shall 104. The exterior surface of the tunnels 145 along with feet 148 located on the foot support piece 146 act as footings to support the transport case 102 off of the floor when the case is in the upright position. The extendable support foot 138 may move between a collapsed and an extended position by merely pulling on the support crossmember 142 to cause the pair of telescoping arms 140 to extend. Similarly, the extendable support foot 138 is returned to the collapsed position by pushing on the support member 142 to collapse the pair of telescoping arms 140 to the collapsed position and store the support crossmember 142 substantially under the case shell 104. When in the extended position, the support crossmember 142 acts as an extended foot support to prevent the support case 102 from toppling over when weight is placed upon the desk shelf 118. When in the extended position, the extendable support foot 138 does not extend completely parallel to the to the bottom panel 108 of the case shell 104. The extendable support foot 138 will extend at a slightly downward angle toward the ground. This enables the extendable support foot 138 to raise the wheels 166 off of the ground to provide a more stable platform for the desk and monitoring components.

Referring now back to FIG. 1, the telescoping monitoring component assembly 114 consists of first and second telescoping members 148 that move between a collapsed position for transport and an extended position for use of associated monitoring components 151 (FIG. 2). The first and second telescoping members 148 may comprise two or more tubes of progressively smaller sizes that telescope within one another as the members 148 are collapsed. A pair of support sleeves 150 extend upward from the bottom panel 108 of the case shell 104 and receive and support the first and second telescoping members 148 to anchor the telescoping monitoring component assembly 114 to the case shell 104. The pair of support sleeves 150 maintain the first and second telescoping members 148 a fixed distance from each other.

Figure 4:
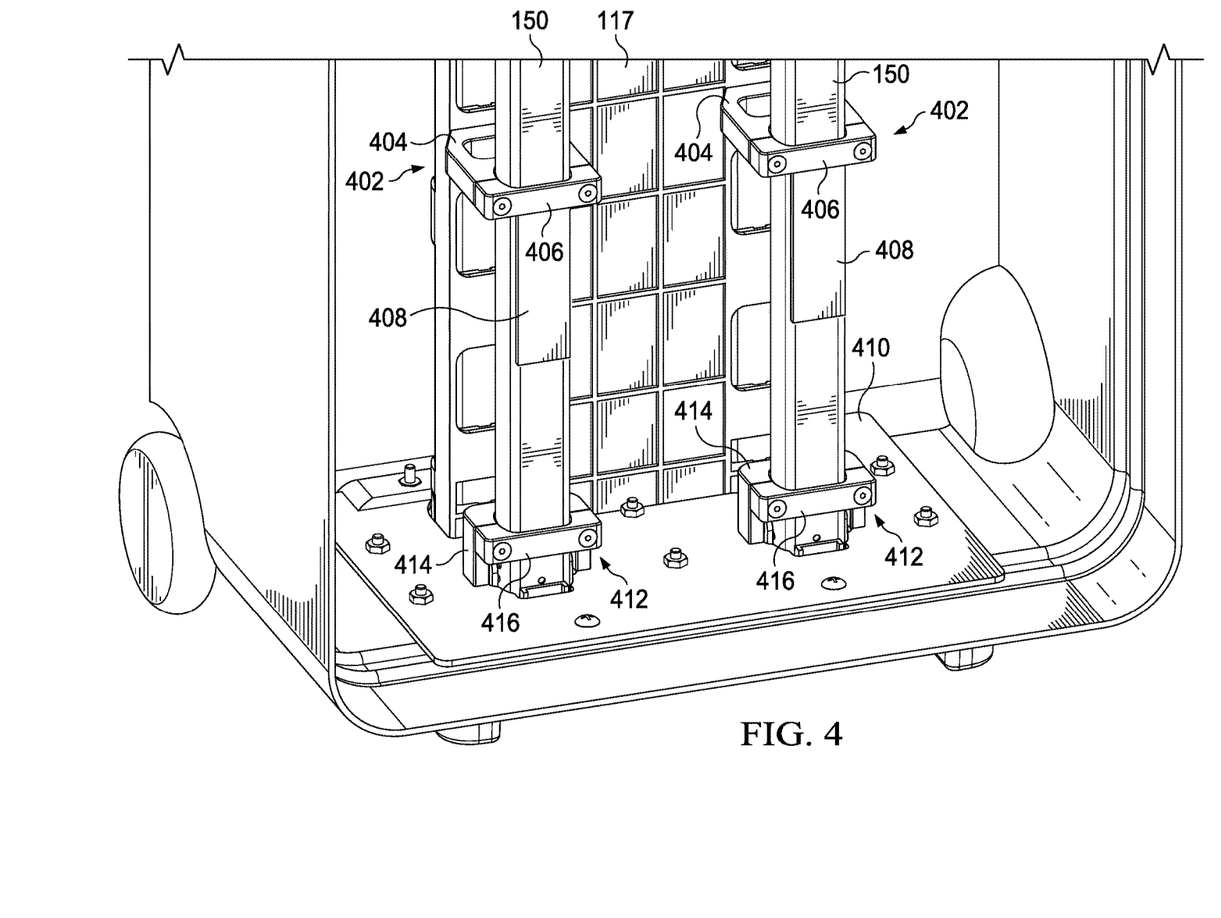
FIG. 4 illustrates a perspective view of the support sleeve configuration.

The support sleeves 150 and the monitoring component assembly 114 are supported and attached to the case shell 104 as illustrated in FIG. 4. A pair of upper stabilizing brackets 402 secures each of the support sleeves 150 to the desk assembly support plate 117. The upper stabilizing brackets 402 consists of a first portion 404 having a first side securely affixed to the desk assembly support plate 117 and defining on its opposite side a slot for receiving the support sleeve 150. A second portion 406 also defines a slot for receiving the support sleeve 150. When the second portion is removeable connected to the first portion 404, using for example, screws, bolts or other type of securing mechanism, the support sleeve 152 is securely affixed therebetween within the slots defined in each of the first portion 404 and second portion 406 of the upper stabilizing bracket 402. Separate upper stabilizing brackets 402 are used to secure each of the support sleeves 150 to the desk assembly support plate 117. Providing additional support from the upper stabilizing brackets 402 is a support plate 408 that is integrated with the second portion 406 of the upper stabilizing bracket and extends downwardly there from. The support plate 408 comprises a rectangular plate and provides additional stabilizing forces to the side of the support sleeve 150 opposite the desk assembly support plate 117.

Additional support to the support sleeves 150 are provided by base interior support plate 410. The base interior support plate 410 defines an opening for each of the first and second telescoping members of the telescoping desk assembly 112 and the telescoping monitoring component assembly 114 to extend therethrough and further defines an opening for going around the desk assembly support plate 117. The base interior support plate 410 is secured to the bottom panel 108 of the case shell 104 using bolts and screws or other type of securing mechanism to the base exterior support plate 144 on the exterior side of the bottom panel 108. Lower stabilizing brackets 412 are integrated with the base interior support plate 410 to provide further support to the support sleeves 150. The lower stabilizing brackets 412 include a first portion 414 that is securely affixed/integrated to the base interior support plate 410. The first portion 414 defines a slot for receiving the support sleeve 150. A second portion 416 of the lower stabilizing bracket 412 is removably connected to the first portion 414 via screws, bolts or other type of securing mechanism. The second portion 416 also defines a slot therein for receiving the support sleeve 150. When the first portion 414 and the second portion 416 of the lower stabilizing bracket 412 are secured together they securely clamped the support sleeves 150 within the slots between the first and second portions of the lower stabilizing brackets 412. The lower stabilizing brackets 412 provide a means for securing the lower portions of the support sleeves 150 to the base interior support plate 410.

Figure 5:
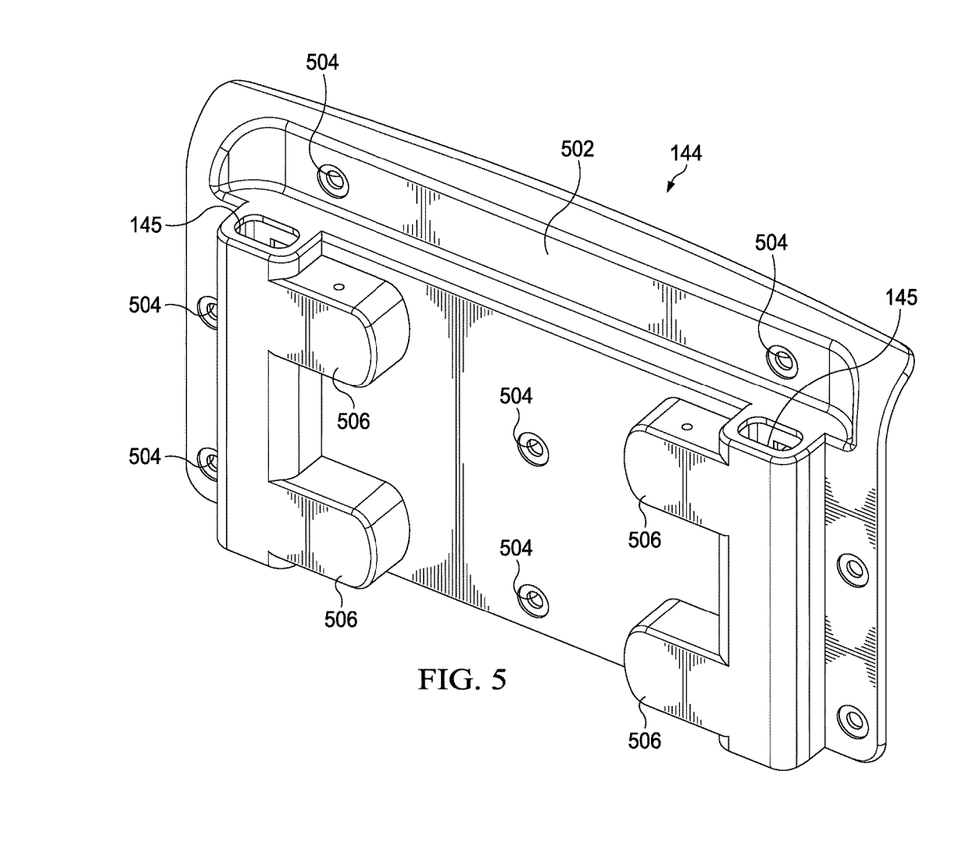
FIG. 5 illustrates a perspective view of the base exterior support plate.

Referring now to FIG. 5, there is more particularly illustrated the base exterior support plate 144. As discussed previously with respect to FIG. 3, the base exterior support plate 144 defines a pair of tunnels 145 for receiving the telescoping arms 140 associated with the extendable support foot 138. A receiving channel 502 is defined for receiving the foot support piece 146 that is secured to the base interior support plate through holes 504 using screws or bolts. The base exterior support member 144 defines four different wells 506 for receiving the ends of the first and second telescoping members of the telescoping desk assembly 112 and the telescoping monitoring component assembly 114. The wells 506 provide for support of the ends of the telescoping members and the exterior surfaces of the wells 506 provide support feet for the base of the transport case 102. The base exterior support plate 144 is secured to the base interior support plate 410 using screws or bolts through holes 504. This also secures the base exterior support plate 144 and the base interior support plate 410 to the bottom panel 108 and the case shell 104 by clamping the bottom panel between each of the base exterior support plate and base interior support plate.

Referring now back to FIGS. 1 and 2, a handle 152 with an actuator button 154 allows the first and second telescoping members 148 to be raised and lowered between the collapsed position and the extended position. The actuator button 154 disengages a locking mechanism that locks the first and second telescoping members 148 into the extended position when the handle 152 is raised from the collapsed position. The locking mechanism automatically engages when the first and second telescoping members 148 are moved to the extended position. The locking mechanism in one embodiment may comprise a spring loaded locking tab or detent that inserts into an opening in the first and second telescoping members 148 as the first and second telescoping members are raised to the extended position. The first and second telescoping members 148 may include one or more intermediate extended positions between the collapsed position and the extended position in which the first and second telescoping members 148 may be configured in a locked position. The actuator button 154 on the handle 152 is also used for disengaging the locking mechanism from these intermediate extended positions.

A component bracket handle 160 is located between the handle 152 and the ends of the telescoping members 148 inserted into support sleeves 150 and slidably engages the telescoping members 149 that are running through the handle 160. The component bracket handle 160 may be moved between a collapsed position and an open position by sliding along the telescoping members 148. The component bracket handle 160 includes an actuator button 162 that disengages a locking mechanism that automatically locks the component bracket handle 160 in the open position. The actuator button 162 when depressed enables the component bracket handle 124 to be moved from the raised position to the lowered position. The locking mechanism may comprise in one embodiment a spring loaded tab or detent mechanism within the handle that is biased to insert within an opening within the first and second telescoping members 148 to automatically lock the component bracket handle 160 in the raised position and to retract from the opening when the actuator button 162 is engaged enabling the component bracket handle to be lowered to the lowered position.

A component support bracket 170 may be mounted to the component bracket handle 160 to enable monitoring components to be connected to the monitoring component support frame 110 and moved between the raised and lowered positions. Thus, by raising the component bracket handle 160 to the raised position, monitoring components connected to the component support bracket 170 may be moved to a use position for carrying out monitoring activities. Similarly, when the system is being transported, monitoring components are moved to a collapsed position and the component bracket handle 160 can be lowered to the lowered position to store monitoring components within the case shell 104. The component bracket handle 160 would comprise the main load bearing component for the component support bracket 170 that supports each of the monitoring components 150 that are contained within the system. The component support bracket 170 may comprise any configuration necessary to support the particular components 150 that are being utilized for monitoring a particular situation. The component support bracket 170 may be changed to provide the capabilities necessary for a particular monitoring system without changing the configuration of the monitoring component support frame 110 described herein. Particular implementations of some aspects of a component support bracket 170 will be more fully described herein below.

In addition to providing for the raising and lowering of the telescoping desk assembly 112 and the telescoping monitoring component assembly 114, the handles 120 and/or 152 may be moved to an extended position and without extending the desk shelf 118 or component bracket 170 may be used as a handle for pulling the transport case 102 as the entire case rolls on an associated set of wheels 166.

Figure 6:
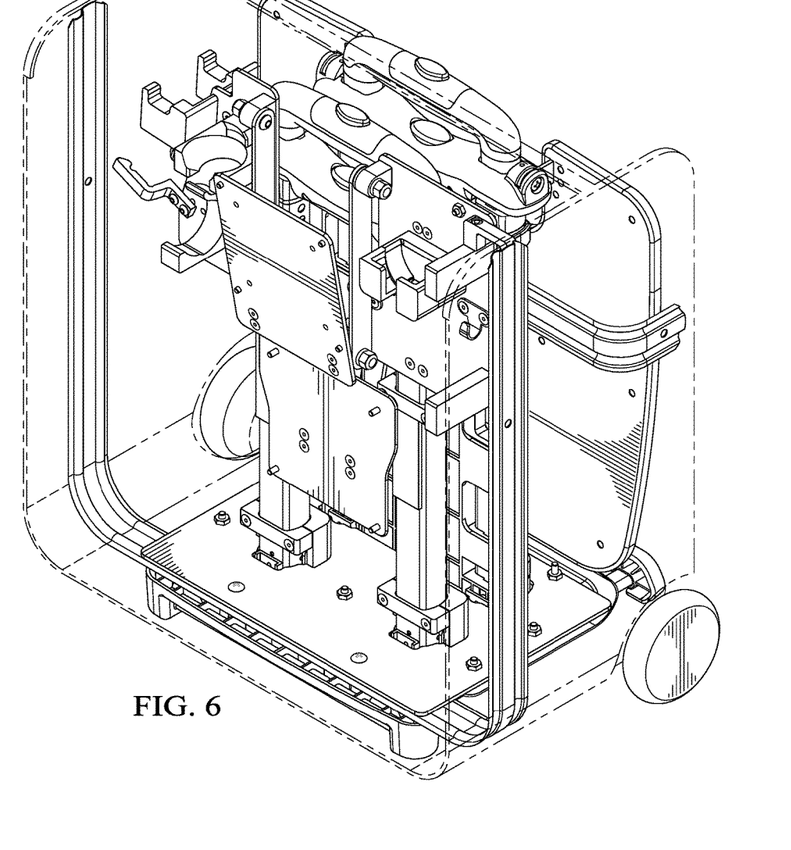
FIG. 6 illustrates a perspective view of the component support system in a collapsed configuration.
Figure 7:
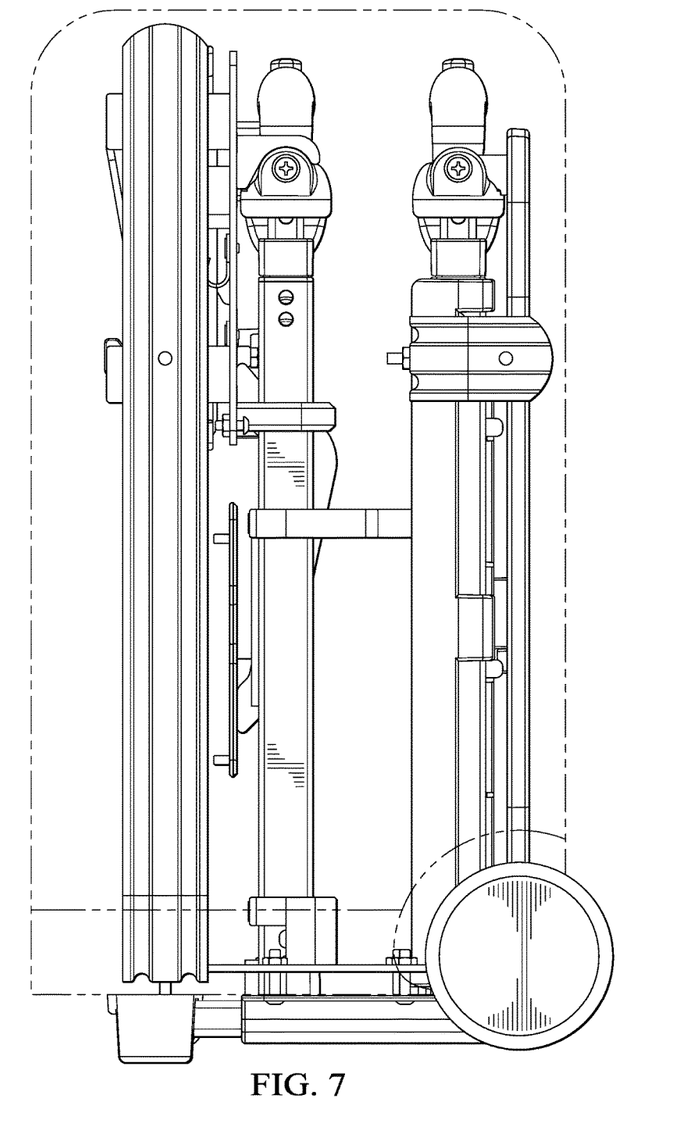
FIG. 7 illustrates a side view of the component support system in a collapsed configuration.

Referring now to FIGS. 6 and 7, there are illustrated a perspective view of the system 102 with the device in a collapsed configuration (FIG. 6) and a side view of the system with the device in the collapsed configuration (FIG. 7). In the collapsed configuration the component support bracket 170 is folded down to be relatively flush with the monitoring component assembly 114. The lowering handle 160 is lowered to a collapsed position and handle 152 is lowered to the collapsed position. Similarly, the desk shelf 118 is lowered to a collapsed position parallel and flush to the desk assembly 112 and the desk handle 124 is lowered to the collapsed position along with handle 120. This allows both the desk assembly 112 and the monitoring component assembly 114 to be closed within that the case shell 104 and associated closure zippers or fasteners may be secured to completely enclose and protect components within the case shall 104. It should be noted that the illustration of FIG. 6 illustrates the case shall without the top front and back panels for illustration purposes, but these components would be present and completely enclose the collapsed assemblies within a protective case shell 104.

Figure 8:
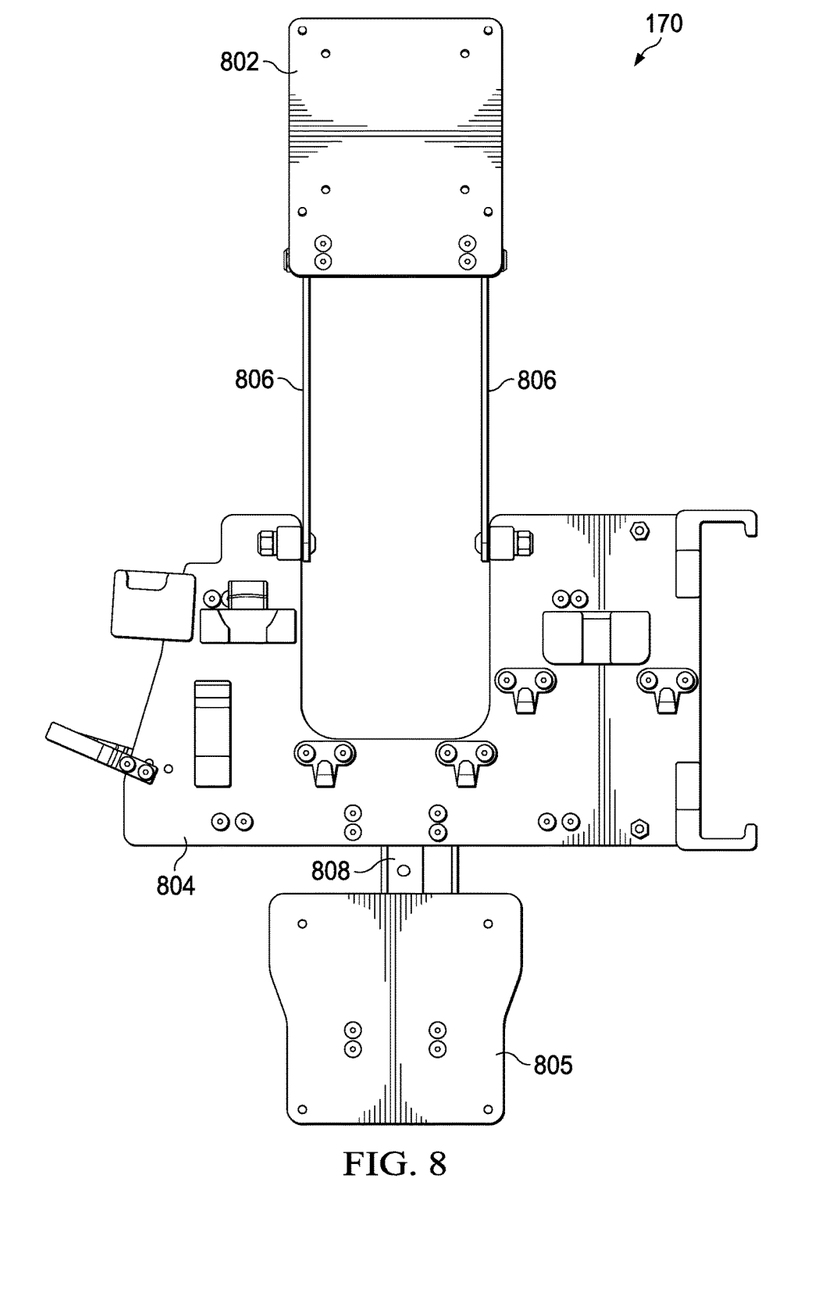
FIG. 8 illustrates one example of a monitoring component support bracket.

Referring now to FIG. 8, there is illustrated one example of the component support bracket 170. In the example of FIG. 8, the component support bracket 170 consists of a first support plate 802, second support plate 804 and a third support plate 806. The second support plate 804 is mounted directly to the component bracket handle 160. The first support plate 802 is pivotally mounted to the second support plate 804 through a pair of pivot arms 806. The pivot arms 806 have a first end pivotally connected to the second support plate 804 and a second end pivotally connected to the first support plate 802. The third support plate 802 is mounted to the second support plate 804 through a connecting member 808. The support plates 802, 804 and 806 may support any number of devices are components. In one embodiment, the first support plate 802 may support a Microsoft® Pro Monitor, the second support plate could support various monitoring and diagnostic tools such as a stethoscope, thermometer, ultrasound device, camera, speaker, blood pressure monitor or other monitoring component and the third support plate 805 may support a Welch Allyn Monitor. A further example of configurations of the support bracket and associated monitoring components may be found in U.S. Provisional Application Nos. 62/488,048 and 62/488,735 entitled PORTABLE MEDICAL STATION, filed on Apr. 20, 2017 and Apr. 22, 2017, which are attached hereto in the appendix.

Figure 9:
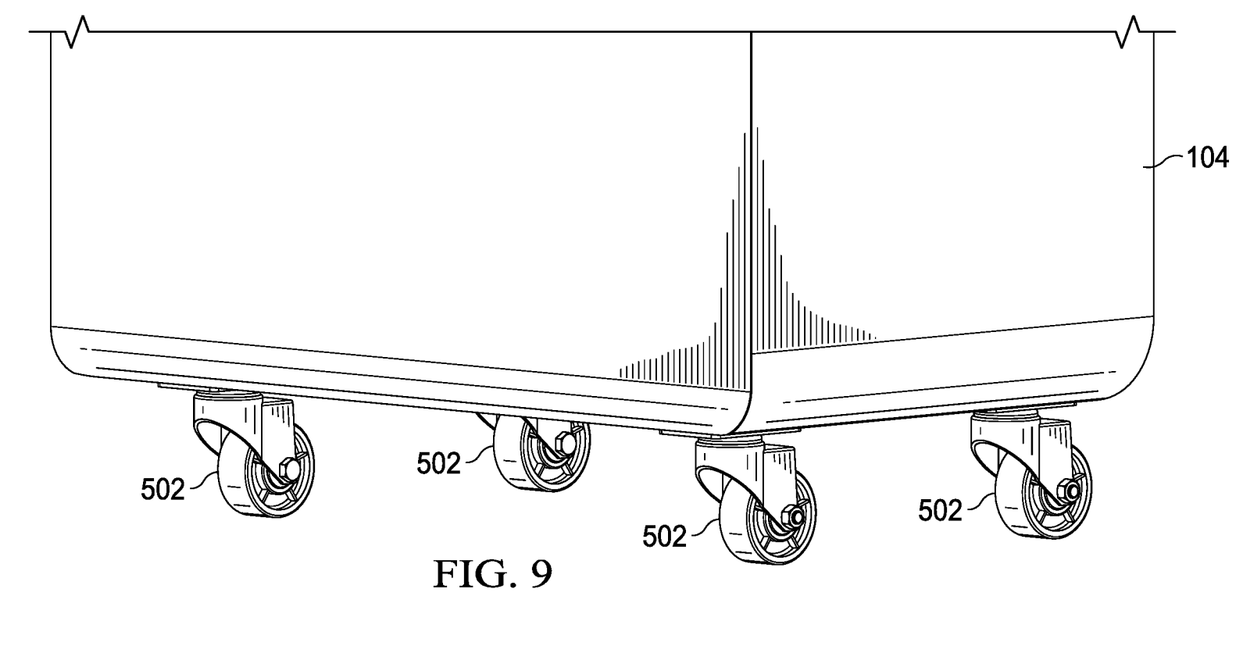
FIG. 9 illustrates an alternative embodiment wherein the system is supported by four caster wheels.

Referring now also to FIG. 9, there is illustrated and alternative embodiment, wherein rather than an extendable support foot 138. The bottom of the case shell 104 includes four completely rotatable caster wheels 902. The caster wheels 902 can rotate 360 degrees and completely support the case shell 104. The caster wheels 902 would also include a locking mechanism to lock the caster wheels in position and prevent the case shell from rolling around when the desk and monitoring components are deployed.

It will be appreciated by those skilled in the art having the benefit of this disclosure that this portable monitoring system transport case provides a system and method for transporting monitoring components in a small transportable configuration that enables the monitoring devices to be taken to remote locations. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A portable transport system for containing and transporting monitoring system components, comprising:
    a case for enclosing the monitoring system components;
    a collapsible desk assembly that telescopes between a collapsed position wherein the collapsible desk assembly is substantially contained within the case and an open position, the collapsible desk assembly including a desk shelf that extends outward from the collapsible desk assembly in the open position and folds down within the case in the collapsed position;
    a collapsible monitoring component assembly that telescopes between a collapsed position wherein the collapsible monitoring component assembly is substantially contained within the case and an open position, the collapsible monitoring component assembly including a component bracket mounting handle for interfacing the monitoring system components with the collapsible monitoring component assembly, the component bracket mounting handle for moving the monitoring system components between a raised position and a lowered position; and
    wherein the collapsible desk assembly and the collapsible monitoring component assembly are contained substantially within the case in the collapsed position.

2. The portable transport system of claim 1, wherein collapsible monitoring component assembly comprises:
    a pair of telescoping members having a first end connected to a base of the case that extend between the collapsed position and the open position; and
    a handle connected to a second end of the pair of telescoping members for moving the pair of telescoping members between the collapsed position and the open position.

3. The portable transport system of claim 2, wherein the collapsible monitoring component assembly further comprises:
    a locking mechanism for automatically locking the collapsible monitoring component assembly into the open position when the collapsible monitoring component assembly is moved to the open position; and
    a first actuator button located in the handle for disengaging the locking mechanism to enable the collapsible monitoring component assembly to move from the open position to the collapsed position.

4. The portable transport system of claim 1, wherein the component bracket mounting handle further comprises:
    a locking mechanism for automatically locking the component mounting handle into the raised position when the component bracket mounting handle is moved from the lowered position to the raised position; and
    an actuator button located in the component bracket mounting handle for disengaging the locking mechanism to enable the component bracket mounting handle to move from the raised position to the lowered position.

5. The portable transport system of claim 1 further including a stability assembly for securing the collapsible desk assembly and the collapsible monitoring component assembly to each other and to the case, the stability assemble further comprising:
- an interior base support plate located on an interior surface of a bottom panel of the case, the interior base support plate defining openings therein to enable the collapsible desk assembly and the collapsible monitoring component assembly to extend therethrough;
- an exterior base support plate located on an exterior surface of the bottom panel of the case, the exterior base support plate defining a plurality of wells into which and end of the collapsible desk assembly and an end of the collapsible monitoring component assembly are inserted; and
- wherein the interior base support plate and the exterior base support plate are secured to each other through the bottom panel using a fastening mechanism.

6. The portable transport system of claim 5 further including:
- a first set of brackets for connecting the collapsible desk assembly to the collapsible monitoring component assembly; and
- a second set of brackets for connecting the collapsible monitoring component assembly to the interior base support plate.

7. The portable transport system of claim 1, wherein including a stabilizing foot comprising:
- a pair of telescoping members having a first end connected to a bottom panel of the case;
- a support foot member connected to the second ends of the pair of telescoping members; and
- wherein the support foot member moves between a closed position located substantially under the case and an open position extending outward from the case under the desk shelf.

8. The portable transport system of claim 1, wherein the collapsible desk assembly further comprises:
- a pair of telescoping members having a first end connected to a base of the case that extend between the collapsed position and the open position;
- a handle connected to a second end of the pair of telescoping members for moving the pair of telescoping members between the collapsed position and the open position;
- a desk handle disposed between the first end of the pair of telescoping members and the handle and having the pair of telescoping members running therethrough in slidable engagement therewith;
- wherein the desk shelf is pivotally connected to the desk handle and adapted to pivot outwardly and upwardly and lock into a position generally orthogonal to the pair of telescoping members; and
- a telescoping member having a first end pivotally connected to an underside of the desk shelf for securing the desk shelf in the position generally orthogonal to the pair of telescoping members and having a second end of the telescoping member pivotally connected to a mounting bracket between the pair of telescoping members.

9. The portable transport system of claim 8 further including a release lever for releasing the desk shelf from a locked open position.

10. The portable transport system of claim 1 further including a stabilizing foot extending outward from the case to stabilize the case and prevent the case from toppling over when the collapsible desk assembly is in the open position.

11. A portable transport system for containing and transporting monitoring system components, comprising:
- a case for enclosing the monitoring system components;
- a collapsible desk assembly that telescopes between a collapsed position wherein the collapsible desk assembly is substantially contained within the case and an open position, the collapsible desk assembly including a desk shelf that extends outward from the collapsible desk assembly in the open position and folds down within the case in the collapsed position, wherein the collapsible desk assembly further comprises:
  - a first pair of telescoping members having a first end connected to a base of the case that extends between the collapsed position and the open position;
  - a first handle connected to a second end of the first pair of telescoping members for moving the first pair of telescoping members between the collapsed position and the open position;
  - a desk handle disposed between the first end of the first pair of telescoping members and the first handle and having the first pair of telescoping members in slidable engagement therewith;
  - wherein the desk shelf is pivotally connected to the desk handle and adapted to pivot outwardly and upwardly and lock into a position generally orthogonal to the first pair of telescoping members; and
  - a telescoping member having a first end pivotally connected to an underside of the desk shelf for securing the desk shelf in the position generally orthogonal to the first pair of telescoping members and having a second end of the telescoping member pivotally connected to a mounting bracket between the first pair of telescoping members;
- a collapsible monitoring component assembly that telescopes between a collapsed position wherein the collapsible monitoring component assembly is substantially contained within the case and an open position, the collapsible monitoring component assembly including, wherein collapsible monitoring component assembly further comprises:
  - a second pair of telescoping members having a first end connected to a base of the case that extend between the collapsed position and the open position;
  - a second handle connected to a second end of the second pair of telescoping members for moving the second pair of telescoping members between the collapsed position and the open position;
  - a component bracket mounting handle for interfacing the monitoring system components with the collapsible component monitoring assembly, the component bracket mounting handle disposed between the first end of the second pair of telescoping members and the second handle and having the second pair of telescoping members in slidable engagement therewith to move the monitoring system components between a raised position and a lowered position;
- wherein the collapsible desk assembly and the collapsible monitoring component assembly are contained substantially within the case in the collapsed position; and
- a stabilizing foot extending outward from the case to stabilize the case and prevent the case from toppling over when the collapsible desk assembly is in the open position.

12. The portable transport system of claim 11, wherein the collapsible monitoring component assembly further comprises:

a locking mechanism for automatically locking the collapsible monitoring component assembly into the open position when the collapsible monitoring component assembly is moved to the open position; and an actuator button located in the second handle for disengaging the locking mechanism to enable the collapsible monitoring component assembly to move from the open position to the collapsed position.

13. The portable transport system of claim 11, wherein the component mounting handle further comprises:

a locking mechanism for automatically locking the mounting handle into the raised position when the component mounting handle is moved from the lowered position to the raised position; and an actuator button located in the component mounting handle for disengaging the locking mechanism to enable the component mounting handle to move from the raised position to the lowered position.

14. The portable transport system of claim 11 further including a stability assembly for securing the collapsible desk assembly and the collapsible monitoring component assembly to each other and to the case, the stability assemble further comprising:

an interior base support plate located on an interior surface of a bottom panel of the case, the interior base support plate defining openings therein to enable the collapsible desk assembly and the collapsible monitoring component assembly to extend therethrough;

an exterior base support plate located on an exterior surface of the bottom panel of the case, the exterior base support plate defining a plurality of wells into which and end of the collapsible desk assembly and an end of the collapsible monitoring component assembly are inserted; and wherein the interior base support plate and the exterior base support plate are secured to each other through the bottom panel using a fastening mechanism.

15. The portable transport system of claim 14 further including:

a first set of brackets for connecting the collapsible desk assembly to the collapsible monitoring component assembly; and a second set of brackets for connecting the collapsible monitoring component assembly to the interior base support plate.

16. The portable transport system of claim 11, wherein the stabilizing foot further comprises:

a pair of telescoping members having a first end connected to a bottom panel of the case;

a support foot member connected to the second ends of the pair of telescoping members; and wherein the support foot member moves between a closed position located substantially under the case and an open position extending outward from the case under the desk shelf.

17. The portable transport system of claim 11 further including a release lever for releasing the desk shelf from a locked open position.

18. The portable transport system of claim 11 further including a stabilizing foot extending outward from the case to stabilize the case and prevent the case from toppling over when the collapsible desk assembly is in the open position.

19. A portable transport system for containing and transporting medical monitoring system components, comprising:

a case for enclosing the medical monitoring system components;

a collapsible desk assembly that telescopes between a collapsed position wherein the collapsible desk assembly is substantially contained within the case and an open position, the collapsible desk assembly including a desk shelf that extends outward from the collapsible desk assembly in the open position and folds down within the case in the collapsed position;

a collapsible medical monitoring component assembly that telescopes between a collapsed position wherein the collapsible medical monitoring component assembly is substantially contained within the case and an open position, the collapsible medical monitoring component assembly including a medical component mounting handle for interfacing the medical monitoring system components with the collapsible medical component monitoring assembly, the medical component mounting handle for moving the medical monitoring system components between a raised position and a lowered position;

wherein the collapsible desk assembly and the collapsible medical monitoring component assembly are contained substantially within the case in the collapsed position; and a stabilizing foot extending outward from the case to stabilize the case and prevent the case from toppling over when the collapsible desk assembly is in the open position.

20. The portable transport system of claim 19, wherein the medical component mounting handle further comprises:

a locking mechanism for automatically locking the medical component mounting handle into the raised position when the medical component mounting handle is moved from the lowered position to the raised position; and an actuator button located in the medical component mounting handle for disengaging the locking mechanism to enable the medical component mounting handle to move from the raised position to the lowered position.

21. The portable transport system of claim 19 further including a stability assembly for securing the collapsible desk assembly and the collapsible medical monitoring component assembly to each other and to the case, the stability assemble further comprising:

an interior base support plate located on an interior surface of a bottom panel of the case, the interior base support plate defining openings therein to enable the collapsible desk assembly and the collapsible medical monitoring component assembly to extend therethrough;

an exterior base support plate located on an exterior surface of the bottom panel of the case, the exterior base support plate defining a plurality of wells into which and end of the collapsible desk assembly and an end of the collapsible medical monitoring component assembly are inserted; and wherein the interior base support plate and the exterior base support plate are secured to each other through the bottom panel using a fastening mechanism.

22. The portable transport system of claim 21 further including:

a first set of brackets for connecting the collapsible desk assembly to the collapsible medical monitoring component assembly; and a second set of brackets for connecting the collapsible medical monitoring component assembly to the interior base support plate.

23. The portable transport system of claim 19, further comprising:
- a pair of wheels on a bottom of the case enabling the case to be rolled from location to location; and
- wherein the stabilizing foot extends outward from the case at an angle slightly downward from a bottom of the case to cause the pair of wheels to raise off the ground when the stabilizing foot extends outward from the case.

\* \* \* \* \*